United States Patent [19]

Sanderson et al.

[11] Patent Number: 4,628,108

[45] Date of Patent: Dec. 9, 1986

[54] PRODUCTION OF 2-SUBSTITUTED-1,3-DIOXOLANES FROM 1,3-DIOXOLANE AND FORMALDEHYDE

[75] Inventors: John R. Sanderson; Ernest L. Yeakey, both of Austin, Tex.

[73] Assignee: Texaco Inc., White Plains, N.Y.

[21] Appl. No.: 683,548

[22] Filed: Dec. 19, 1984

[51] Int. Cl.$^4$ ........................................... C07D 317/00
[52] U.S. Cl. ................................................. 549/453
[58] Field of Search ......................................... 549/453

[56] References Cited

U.S. PATENT DOCUMENTS

| 2,140,938 | 12/1938 | McNamee et al. | 549/453 |
| 2,862,978 | 12/1958 | Skanner et al. | 549/453 |
| 4,200,765 | 4/1980 | Goetz | 549/449 |
| 4,337,371 | 6/1982 | Kollar | 568/852 |

FOREIGN PATENT DOCUMENTS

| 1957621 | 5/1971 | Fed. Rep. of Germany | 549/453 |
| 488327 | 7/1938 | United Kingdom | 549/453 |
| 975704 | 10/1978 | U.S.S.R. | |

OTHER PUBLICATIONS

"A Free-Radical Reaction of Primary and Secondary Alcohols with Formaldehyde", O. Yano, *J. Org. Chem.* 30, 2429 (1965).

"Oxygen Promoted Addition of 1,3-Dioxolane to Electron Deficient Alkenes", Watanabe et al., *Bull Chem Soc Jpn* 56, 1428-30, (1983), vol. 56, No. 5.

*Primary Examiner*—Ethel G. Love
*Attorney, Agent, or Firm*—Jack H. Park; Kenneth R. Priem

[57] ABSTRACT

It has been surprisingly discovered in accordance with the present invention that when 1,3-dioxolane is reacted with formaldehyde in the presence of an organic peroxide and an ionizable, at least sparingly soluble metal salt, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxyalkyl-1,3-dioxolanes. 2-Hydroxyalkyl-1,3-dioxolanes are hydrolyzed with comparative ease to ethylene glycol and the corresponding glycol aldehyde (CHO—$CH_2$—OH). The glycol aldehyde in turn can be catalytically hydrogenated to form additional quantities of ethylene glycol.

14 Claims, No Drawings

PRODUCTION OF 2-SUBSTITUTED-1,3-DIOXOLANES FROM 1,3-DIOXOLANE AND FORMALDEHYDE

BACKGROUND OF THE INVENTION

1. Technical Field of the Invention

This invention relates to the manufacture of 2-substituted-1,3-dioxolanes. More particularly, this invention relates to a method wherein 1,3-dioxolane is reacted with formaldehyde in the presence of an organic peroxide and an ionizable, at least sparingly soluble metal salt initiator under non-acidic conditions to provide 2-hydroxymethyl-1,3-dioxolane and 2-hydroxymethyl-oxymethylene-1,3-dioxolanes. The 2-hydroxymethyl-1,3-dioxolane is useful as a raw material for the manufacture of ethylene glycol. The hydroperoxide is prepared from the 1,3-dioxolane in accordance with a preferred form of the present invention.

2. Prior Art

Kollar U.S. Pat. No. 4,337,371 discloses a method for the preparation of ethylene glycol wherein methanol and formaldehyde are reacted in the presence of an organic peroxide and water to provide ethylene glycol. In a technical article Oyama discloses the free-radical reaction of primary and secondary alcohols such as methanol, 2-propanol, ethanol, 2-butanol and 3-methyl-2-butanol with formaldehyde, and t-butyl peroxide to provide glycols (*J. Org. Chem.*, 30, 2429 (1965). Watanabe et al. in an article in *Bull. Chem. Soc. Jpn.*, 56, 1428–1430 (1983), Vol. 56, No. 5 disclose the reaction of 1,3-dioxolane with electron-deficient alkenes such as diethyl maleate, maleic anhydride, etc. Russian Author's Certificate No. 975,704 (Imashev et al.) discloses a method wherein 1,3-dioxolane is oxidized with molecular oxygen at a temperature of about 10° to 60° C. to provide ethylene glycol monoformate as a principle reaction product.

RELATED COPENDING PATENT APPLICATIONS

Copending coassigned Sanderson et al. U.S. patent application Ser. No. 06/683,441, filed Dec. 19, 1984 (filed of an even date herewith), discloses a method wherein 1,3-dioxolane is reacted with formaldehyde under non-acidic conditions to provide 2-hydroxymethyl-1,3-dioxolane.

Copending coassigned Sanderson et al. U.S. patent application Ser. No. 06/683,549, filed Dec. 19, 1984 (filed of an even date herewith), discloses the air oxidation of 1,3-dioxolane in the presence of an initiator to provide 2-hydroperoxy-1,3-dioxolane.

Copending coassigned Yeakey et al. U.S. patent application Ser. No. 06/683,546, filed Dec. 19, 1984 (of an even date herewith), discloses a method wherein dimethoxymethane is reacted with paraformaldehyde in the presence of an organic peroxide to provide an ethylene glycol precursor.

SUMMARY OF THE INVENTION

It has been surprisingly discovered in accordance with the present invention that when 1,3-dioxolane is reacted with formaldehyde under non-acidic conditions in the presence of an organic peroxide initiator and an ionizable, at least sparingly soluble metal salt, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxyalkyl-1,3-dioxolanes, such as 2-hydroxymethyl-1,3-dioxolane. The dioxolanes are hydrolyzed with comparative ease to ethylene glycol and the corresponding glycol aldehyde (CHO—CH$_2$—OH). The glycol aldehyde in turn can be catalytically hydrogenated to form additional quantities of ethylene glycol.

In accordance with a preferred embodiment of the present invention, 1,3-dioxolane is oxidized to form the corresponding hydroperoxide, which is then used, in conjunction with a metal salt, to initiate the reaction of 1,3-dioxolane with formaldehyde to form the 2-hydroxyalkyl-1,3-dioxolane, which, in turn, is hydrolyzed to form ethylene glycol and the corresponding glycol aldehyde. The glycol aldehyde, in its turn, is hydrogenated to form an additional quantity of ethylene glycol.

The overall sequence is illustrated by the following equations wherein the 1,3-dioxolane nucleus is schematically indicated, i.e.:

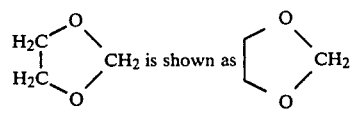

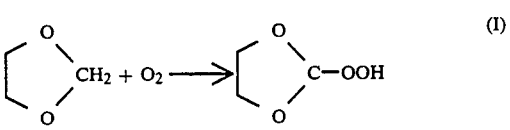
(I)

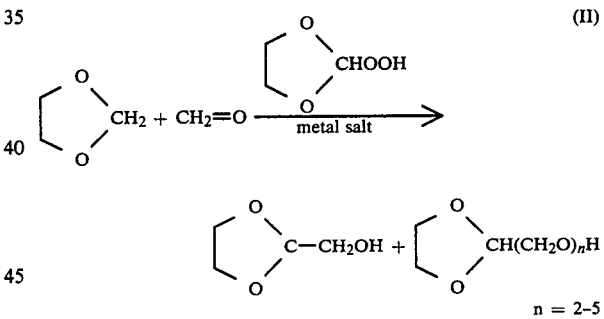
(II)

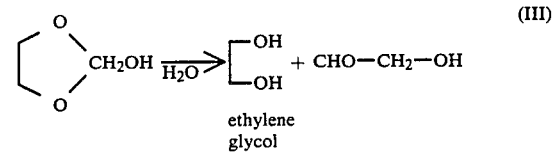
n = 2–5

(III)

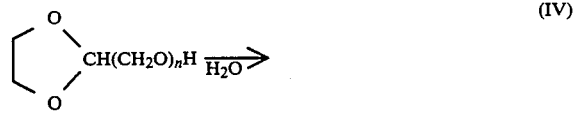
ethylene glycol (IV)

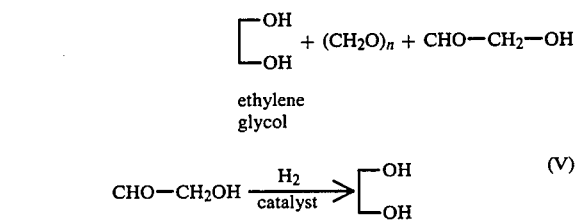
ethylene glycol (V)

DETAILED DESCRIPTION OF THE INVENTION

Starting Materials

The starting materials for the present invention are 1,3-dioxolane, formaldehyde, an organic peroxide and a metal salt.

Formaldehyde may be employed in its conventional form, as an aqueous formalin solution, in "inhibited" methanol solution as paraformaldehyde, or as trioxane.

The organic peroxide employed in the process of the present invention is preferably 2-hydroperoxy-1,3-dioxolane. The 2-hydroperoxy-1,3-dioxolane can be prepared in the manner disclosed in copending Sanderson et al. application Ser. No. 06/683,549, filed Dec. 19, 1984 (of an even date herewith) and entitled "Production of 2-Hydroperoxy-1,3-Dioxolane". However, other organic hydroperoxides can be used, if desired, such as tert.-butyl hydroperoxide, ethylbenzyl hydroperoxide, cumyl hydroperoxide, etc. Suitably, from about 0.1 wt.% to about 10 wt.% of the hydroperoxide is used, based on the weight of the dioxolane feed.

The ionizable, at least sparingly soluble metal salt is used as an initiator. It is suitably a metal salt of an inorganic acid or an organic carboxylic acid, such as a salt of a heavy metal, preferably a group VIIIb heavy metal. Still more preferably, the salt is an ionizable, at least sparingly soluble cobalt II salt of an organic compound, such as cobalt nitrate, cobalt chloride, cobalt hexanoate, cobalt benzoate, cobalt cyclohexane butyrate, cobalt oxalate, cobalt octoate, cobalt acetate, cobalt naphthenate, cobalt acetylacetonate, etc. However, other metal salts may be used, if desired, such as for example, chromium acetate, iron acetylacetonate, iron nitrate, diammonium azium nitrate, nickel acetylacetonate, etc. From about 0.0001 to about 5.0 wt.% of metal salt is preferably used, based on the 1,3-dioxolane feedstock.

Reaction Conditions

The desired products of the present invention, 2-hydroxyalkyl-1,3-dioxolanes, are an equimolar addition product of formaldehyde and 1,3-dioxolane. However, a molar excess of either of the reactants may be used, if desired. Preferably, formalin is used, and is used in a molar excess (e.g., from about 1 to about 5 moles of formaldehyde per mole of 1,3-dioxolane).

The organic peroxide is suitably used in an amount ranging from about 0.1 to about 10 wt.%, based on the 1,3-dioxolane. More preferably, from about 2 to about 5 wt.% of the organic peroxide is used.

The reaction is suitably conducted at a temperature within the range of about 80° to about 250° C., and more preferably, within the range of about 80° to about 150° C.

The reaction is preferably conducted at atmospheric pressure. Superatmospheric or subatmospheric pressures may be used if desired, but there is no particular advantage in doing so.

Reaction times of from about 0.5 to about 10 hours may be employed with satisfactory results. More preferably, the reaction time will be within the range of about 1 to about 5 hours.

The reaction can be conducted in inert solvent solution with a solvent such as acetonitrile, t-butyl alcohol, monochlorobenzene, benzene, etc. but there is no particular advantage in doing so.

At the end of the reaction, the reaction mixture may be separated into components by any suitable technique such as filtration, distillation, solvent extraction, etc.

As indicated earlier, the 2-hydroxymethyl-1,3-dioxolane can be hydrolyzed to provide ethylene glycol and glycolaldehyde under conditions as disclosed, for example in J. D. Roberts, M. C. Caserio, "Basic Principles of Organic Chemistry", W. A. Benjamin, Inc., New York, 1965. See page 443. The glycolaldehyde may also be catalytically hydrogenated to form additional quantities of ethylene glycol under conditions of the type disclosed by H. O. House, "Modern Synthetic Reactions", 2nd Ed., W. A. Benjamin, Inc., 1972. See Chapter 1 and references therein.

SPECIFIC EXAMPLES

Example 1

A 250 ml flask equipped with water-cooled condenser, magnetic stirrer, heating mantle, thermometer (Thermo-O-Watch), and dropping funnel was charged with 50 ml 1,3-dioxolane, 50 g paraformaldehyde and additive. The mixture was heated to a gentle reflux and a hydroperoxide/dioxolane mixture added over several hours. [The hydroperoxide/dioxolane mixture was prepared by oxidizing the dioxolane with air under various conditions.] At the end of the reaction, the mixture was cooled to ambient temperature and the solid paraformaldehyde filtered off. The products were determined by GC. The results are summarized in the following tables. A comparison example is included.

TABLE I

| | | | | | | |
|---|---|---|---|---|---|---|
| Reaction of 1,3-Dioxolane with Formaldehyde | | | | | | |
| Notebook Number | 1,3-Dioxolane (ml) | Paraformaldehyde (g) | 2-Hydroperoxy 1,3-dioxolane conc. (wt. %) | (ml) | Catlayst | (g) |
| 5831-66 | 65 | 5.0 | 3.73 | 15 | Co(oct.)$_2$ | 0.24 |
| 5831-65 | 65 | 5.0 | 6.77 | 15 | Fe(NO$_3$)$_3$ | 0.10 |
| 5831-64 | 65 | 5.0 | 6.77 | 15 | Co(oct.)$_2$ | 0.24 |
| 5831-63 | 65 | 5.0 | 6.77 | 15 | Co(oct.)$_2$ | 0.24 |
| 5831-62 | 65 | 5.0 | 6.77 | 15 | Fe(NO$_3$)$_3$ | 0.10 |
| 5831-52 | 50 | 5.0 | 3.50 | 30 | Fe(NO$_3$)$_3$ | 0.12 |
| 5831-51 | 50 | 5.0 | 3.50 | 30 | Co(oct.)$_2$ | 0.12 |
| 5831-49 | 50 | 5.0 | 4.38 | 30 | Co(oct.)$_2$ | 0.12 |
| 5831-48 | 65 | 5.0 | 4.38 | 15 | Co(oct.)$_2$ | 0.12 |
| 5831-47 | 0 | 5.0 | 0.33 | 50 | Co(oct.)$_2$ | 0.12 |
| 5831-41 | 30 | 5.0 | 3.89 | 50 | Co(oct.)$_2$ | 0.12 |
| 5831-40 | 30 | 5.0 | 1.0 | 50 | Co(oct.)$_2$ | 0.12 |
| 5831-67 | 65 | 5.0 | 3.73 | 15 | Ce(NH$_4$)$_2$(NO$_3$)$_6$ | 0.21 |
| 5831-69 | 65 | 5.0 | 3.73 | 15 | Co(oct.)$_2$ | 0.24 |
| 5831-70 | 65 | 5.0 | 3.73 | 15 | Ni(OAc)$_2$ | 0.25 |

TABLE II

Reaction of 1,3-Dioxolane with Formaldehyde

| Notebook Number | Time (Hr) | Temp (°C.) | Ethyl Formate | Ethylene Glycol | 2-Hydroxy 1,3-dioxolane | A | B | Ethylene Carbonate |
|---|---|---|---|---|---|---|---|---|
| 5831-66 | 5.5 | 60 | 0.455 | 0.098 | 4.450 | 2.219 | 0.124 | 0.842 |
| 5831-65 | 6.5 | 50–55 | 0.007 | 0.008 | 4.687 | 0.096 | — | 0.423 |
| 5831-64 | 6.5 | 60–65 | 0.601 | 0.100 | 4.582 | 2.315 | 0.179 | 0.969 |
| 5831-63 | 6.1 | 55 | 0.492 | 0.079 | 7.063 | 1.737 | — | 1.237 |
| 5831-62 | 6.1 | 60 | 0.013 | 0.005 | 4.762 | 0.386 | — | 0.313 |
| 5831-52 | 8.0 | 75 | 0.869 | 0.009 | 6.843 | 4.143 | 0.617 | 1.338 |
| 5831-51 | 8.0 | 75 | 0.031 | 0.079 | 5.487 | 0.148 | — | 0.643 |
| 5831-49 | 8.0 | 75 | 0.961 | 0.035 | 7.358 | 3.423 | 0.393 | 1.586 |
| 5831-48 | 6.0 | 75 | 0.653 | 0.172 | 4.262 | 2.827 | 0.366 | 0.971 |
| 5831-47 | 6.0 | 75 | — | 0.021 | 0.651 | 0.082 | — | 1.465 |
| 5831-41 | 8.0 | 75 | 0.006 | 0.142 | 6.966 | 0.794 | — | 1.034 |
| 5831-40 | 3.0 | 75 | 0.013 | 0.070 | 7.730 | 0.953 | — | 1.163 |
| 5831-67 | 5.5 | 60 | 0.020 | 0.006 | 3.794 | 0.052 | — | 0.503 |
| 5831-69 | 6.5 | 60 | 0.349 | 0.094 | 4.138 | 1.903 | 0.030 | 0.867 |
| 5831-70 | 6.5 | 60 | 0.083 | 0.135 | 4.876 | 0.067 | 0.032 | 0.948 |

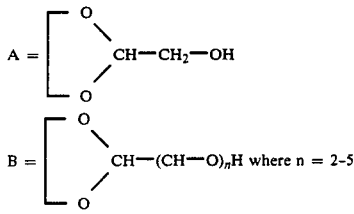

$$B = \begin{bmatrix} O \\ \diagdown \\ \diagup \\ O \end{bmatrix} CH-(CH-O)_nH \text{ where } n = 2-5$$

The data shown in Table I and Table II illustrate the reaction of 1,3-dioxolane with formaldehyde under various conditions: temperature, initiator (hydroperoxide), and metal salt concentration and different metal salts. Ce and Ni salts do not appear to be as effective as some of the other metal salts.

Example 2

1,3-Dioxolane (80 ml), paraformaldehyde (10 g) and di-tert-butyl peroxide (3.00 ml) were charged to a 300 cc. stainless steel autoclave equipped with a magne drive stirrer. The autoclave was heated slowly (over one hour) to the desired temperature and held at this temperature for the desired time. The autoclave was cooled to ambient temperature and the solid paraformaldehyde filtered from the reaction mixture. The reaction conditions, etc., are shown in Table III.

obtained thus lowering the selectivity to the desired products.

Example 3

Procedure

A 250 ml flask equipped with water-cooled condenser, magnetic stirrer, heating mantle, thermometer (Therm-O-Watch), and dropping funnel was charged with 50 ml, 1,3-dioxolane, 10 g paraformaldehyde and additive. The mixture was heated to a gentle reflux and a TBHP/dioxolane mixture added over several hours. [The TBHP/dioxolane mixture was prepared by adding 3.00 ml 65% TBHP/TBA to 30 ml 1,3-dioxolane]. At the end of the reaction, the mixture was cooled to ambient temperature and the solid paraformaldehyde filtered off. The products were determined by GC. The results are summarized in the following Tables IV and V. A

TABLE III

1,3-DIOXOLANE WITH FORMALDEHYDE

| Notebook Number | Time (Hr) | Temp (°C.) | Ethanol | Ethyl Formate | Glycol Ether Acetates | $\begin{bmatrix} O \\ \diagdown \\ \diagup \\ O \end{bmatrix} CHCH_2-OH$ | $\begin{bmatrix} O \\ \diagdown \\ \diagup \\ O \end{bmatrix} CH(CH_2-O)_n-H^d$ |
|---|---|---|---|---|---|---|---|
| 5807-85 | 2 | 180 | 4.14 | 16.60 | 1.44 | 8.98 | 3.85 |
| 5807-84 | 3 | 160 | 3.39 | 17.52 | 1.67 | 9.97 | 4.24 |
| 5807-83 | 5 | 140 | 1.46 | 16.16 | 2.09 | 12.10 | 4.07 |
| 5807-48 | 2 | 130 | — | — | — | — | — |
|  | 2 | 140 | 1.48 | 12.11 | 2.17 | 13.94 | 5.06 |

$c=$ Products determined on sample after solid paraformaldehyde had been removed.
$d=$ n = 2-5

As will be seen from Table III, moderate yields of 2-hydroxymethyl-1,3-dioxolane were obtained in all of the runs, but moderate yields of ethyl formate were also comparison example is included.

TABLE IV

Reaction of 1,3-Dioxolane with Formaldehyde

| Notebook Number | 1,3-Dioxolane (ml) | Paraformaldehyde (g) | TBHP$^a$ (ml 65%) | Additive | Time (Hr) | Temp (°C.) |
|---|---|---|---|---|---|---|
| 5831-6 | 50 (+30) | 10.0 | 3.00 | cobalt octate | 7 | 75 |

TABLE IV-continued

Reaction of 1,3-Dioxane with Formaldehyde

| Notebook Number | 1,3-Dioxolane (ml) | Paraformaldehyde (g) | TBHP[a] (ml 65%) | Additive | Time (Hr) | Temp (°C.) |
|---|---|---|---|---|---|---|
| 5831-10 | 50 (+30) | 10.0 | 3.00 | (5 d) Fe complex (0.05 g) | 6 | 75 |
| 5831-12 | 50 (+30) | 10.0 | 3.00 | cobalt octate (10 d) | 7 | 75 |
| 5831-22 | 50 (+30) | 10.0 | 3.00 | Fe(AcAc)$_3$ (0.05) | 5 | 75 |
| 5831-24 | 50 (+30) | 10.0 | 3.00[d] | cobalt octate (10 d) | 8 | 75 |
| 5831-25 | 50 (+30) | 10.0 | 3.00 | chromium acetate (0.05 g) | 7 | 75 |
| 5831-27 | 50 (+30) | 10.0 | 6.00 | cobalt octate (10 d) | 7 | 75 |

TABLE V

Reaction of 1,3-Dioxolane with Formaldehyde
Products, (Area %)

| Notebook | TBA | Ethyl Formate | Glycol Ether Acetates | 2-Hydroxy-methyl-1,3-dioxolane | $\begin{bmatrix} O \\ \phantom{x} \diagdown \\ \phantom{xx} CH(CH_2-O)_n-H^c \\ \phantom{x} \diagup \\ O \end{bmatrix}$ |
|---|---|---|---|---|---|
| 5831-6 | 3.16 | Trace | 1.69 | 4.08 | 0.94 |
| 5831-10 | 3.39 | sh[b] | 1.67 | 2.72 | 1.50 |
| 5831-12 | 3.13 | 0.64 | 1.54 | 9.60 | 1.66 |
| 5831-22 | 3.42 | — | 0.86 | 0.38 | — |
| 5831-24 | 3.04 | 0.41 | 1.64 | 4.04 | 0.64 |
| 5831-25 | 2.23 | 0.28 | 0.58 | 2.76 | 0.43 |
| 5831-27 | 4.66 | 0.76 | 2.27 | 6.18 | 1.28 |

[a]TBHP = tert-butylhydroperoxide; DTBP = di-tert-butylperoxide
[b]shoulder on tert-butylalcohol peak
[c]n = 2-5
[d]added all at once Note from Tables IV and V that the formation of ethyl formate by-products was virtually eliminated when the reaction was catalyzed with tert-butyl hydroperoxide promoted with cobalt octate. In contrast, the results from Table III show that the yield of ethyl formate was significant.

The foregoing examples are given by way of illustration and are not intended as limitations on the scope of the present invention, which is defined by the appended claims.

What is claimed is:

1. A method for the preparation of 2-hydroxyalkyl-1,3-dioxolanes which comprises reacting 1,3-dioxolane under non-acidic conditions with formaldehyde in the presence of a hydroperoxide and a metal salt.

2. A method as in claim 1, wherein the metal salt is an ionizable, at least sparingly soluble cobalt II salt of an organic compound and the hydroperoxide is tert-butyl hydroperoxide.

3. A method as in claim 2, wherein the cobalt salt is cobalt octoate.

4. A method as in claim 1, for the preparation of 2-hydroxymethyl-1,3-dioxolane.

5. A method as in claim 4, wherein the metal is a metal from group VIIIb of the periodic table.

6. A method as in claim 5, wherein the group VIIIb metal is cobalt.

7. A method as in claim 6, wherein the metal salt is cobalt octoate.

8. A method which comprises the steps of reacting 1,3-dioxolane with from about 0.5 to about 5 moles of formaldehyde per mole of dioxolane under non-acidic conditions at a temperature within the range of about 80° to about 250° C. in the presence of from about 0.01 to about 10 wt.% of tert-butyl hydroperoxide and 0.0001 to 5 wt.% of a cobalt salt, based on the 1,3-dioxolane and recovering 2-hydroxyalkyl-1,3-dioxolanes from the products of the reaction, said cobalt salt being an ionizable, at least sparingly soluble cobalt II salt.

9. A method as in claim 8, wherein the cobalt salt is an at least sparingly soluble cobalt salt of an organic carboxylic acid.

10. A method as in claim 8, wherein the cobalt salt is cobalt octoate.

11. A method which comprises the steps of reacting 1,3-dioxolane with from about 0.5 to about 5 moles of formaldehyde per mole of dioxolane at a temperature within the range of about 80° to about 250° C. in the presence of from about 0.1 to about 10 wt.% of an organic peroxide and about 0.0001 to about 5 wt.% of a metal salt of an organic carboxylic acid, based on the 1,3-dioxolane and recovering 2-hydroxymethyl-1,3-dioxolane from the products of the reaction.

12. A method as in claim 11, wherein the metal of the metal salt is a metal from group VIIIb of the periodic table.

13. A method as in claim 12, wherein the group VIIIb metal is cobalt.

14. A method as in claim 13, wherein the metal salt initiator is cobalt octoate.

* * * * *